US006602196B2

(12) United States Patent
Suzuki et al.

(10) Patent No.: US 6,602,196 B2
(45) Date of Patent: Aug. 5, 2003

(54) ULTRASONIC IMAGING APPARATUS

(75) Inventors: Yoichi Suzuki, Tokyo (JP); Shinichi Amemiya, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/170,031

(22) Filed: Jun. 12, 2002

(65) Prior Publication Data

US 2003/0018264 A1 Jan. 23, 2003

(30) Foreign Application Priority Data

Jun. 19, 2001 (JP) .......................................... 2001-184678

(51) Int. Cl.[7] ................................................. A61B 8/06
(52) U.S. Cl. ....................................... 600/455; 600/441
(58) Field of Search ................................. 600/447, 454, 600/455, 445, 444, 437, 443, 441; 128/916; 73/626

(56) References Cited

U.S. PATENT DOCUMENTS 5,520,184 A * 5/1996 Ri ............................... 600/437
5,840,033 A * 11/1998 Takeuchi .................... 600/443
5,902,244 A * 5/1999 Kobayashi et al. ......... 600/447

FOREIGN PATENT DOCUMENTS

JP 03272749 * 3/1990

* cited by examiner

Primary Examiner—Marvin M. Lateef
Assistant Examiner—Ruby Jain
(74) Attorney, Agent, or Firm—Carl B. Horton, Esq.; Armstrong Teasdale LLP

(57) ABSTRACT

In order to make both the maintenance of a scan range and a frame rate for ultrasonic imaging and high definition of an image compatible with each other, a sound-ray density for scan is made nonuniform, and a sound-ray density is rendered dense at a required portion and coarse at portions other than the portion.

20 Claims, 12 Drawing Sheets

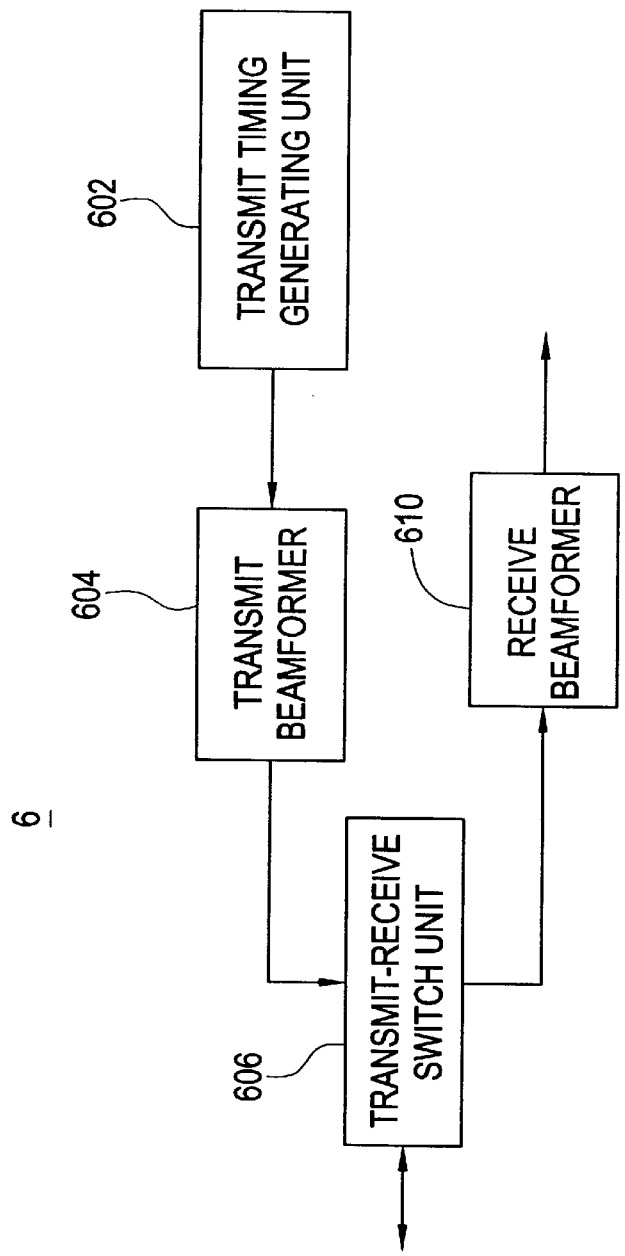
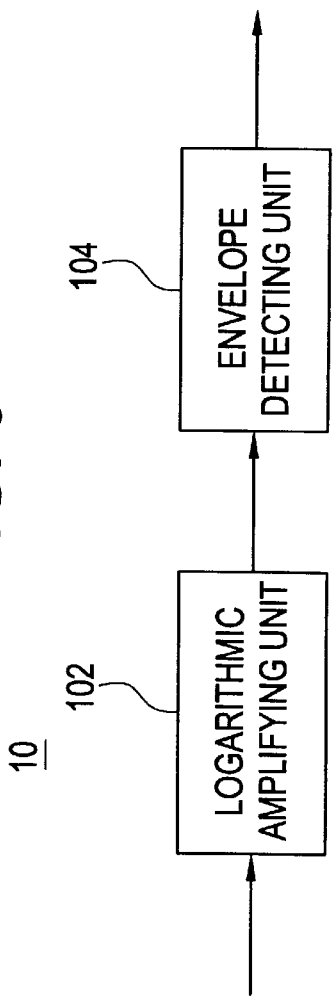

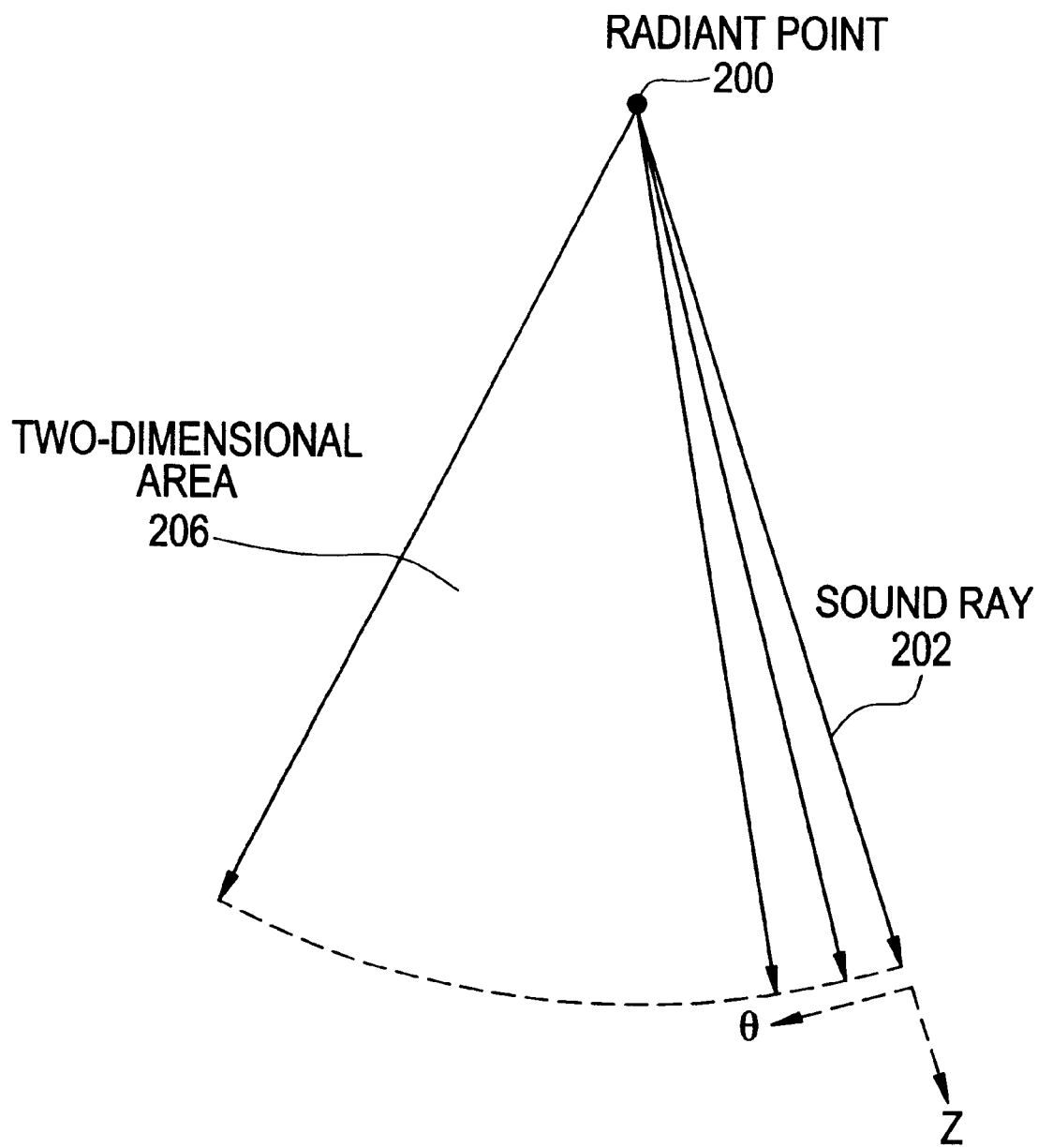

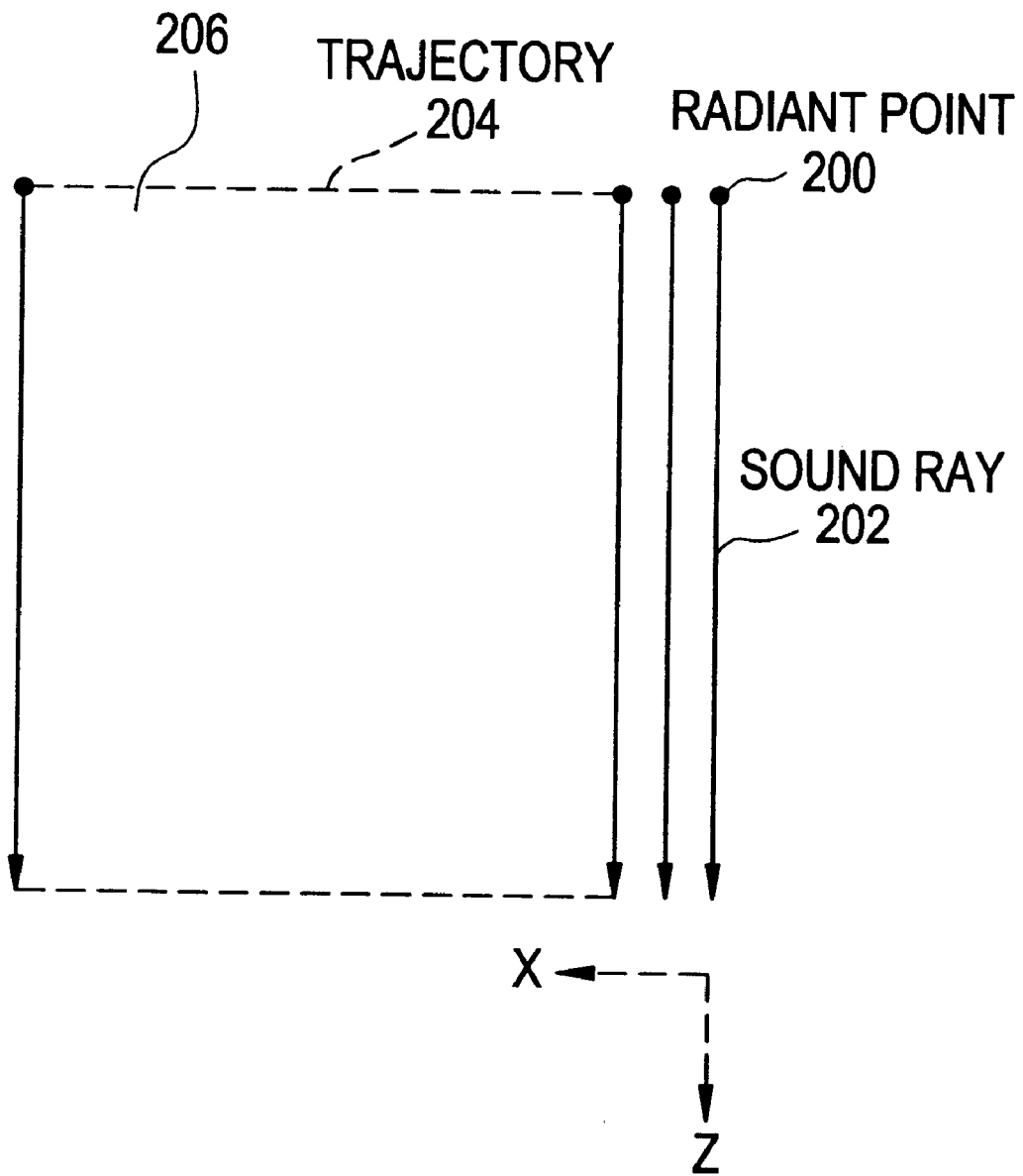

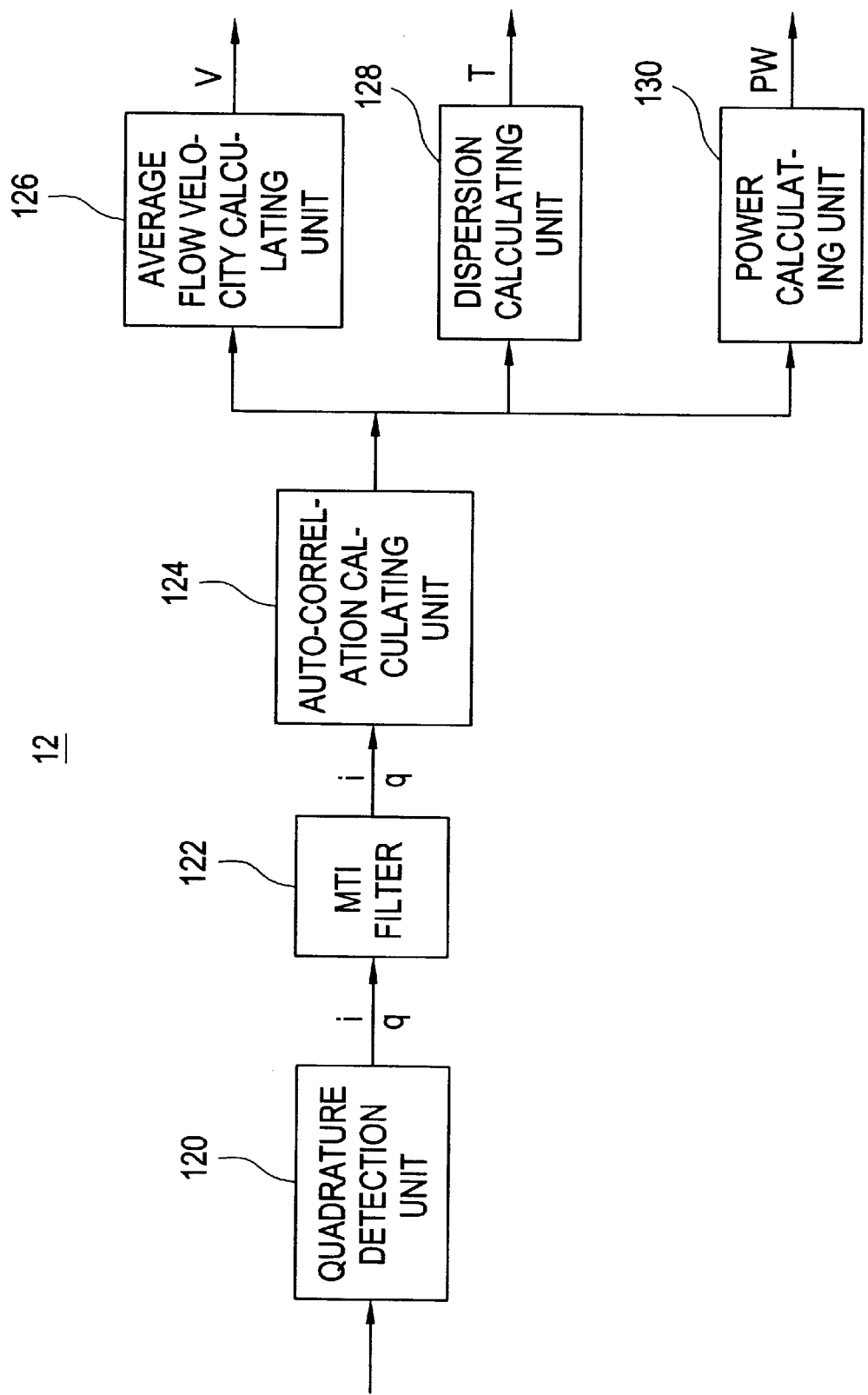

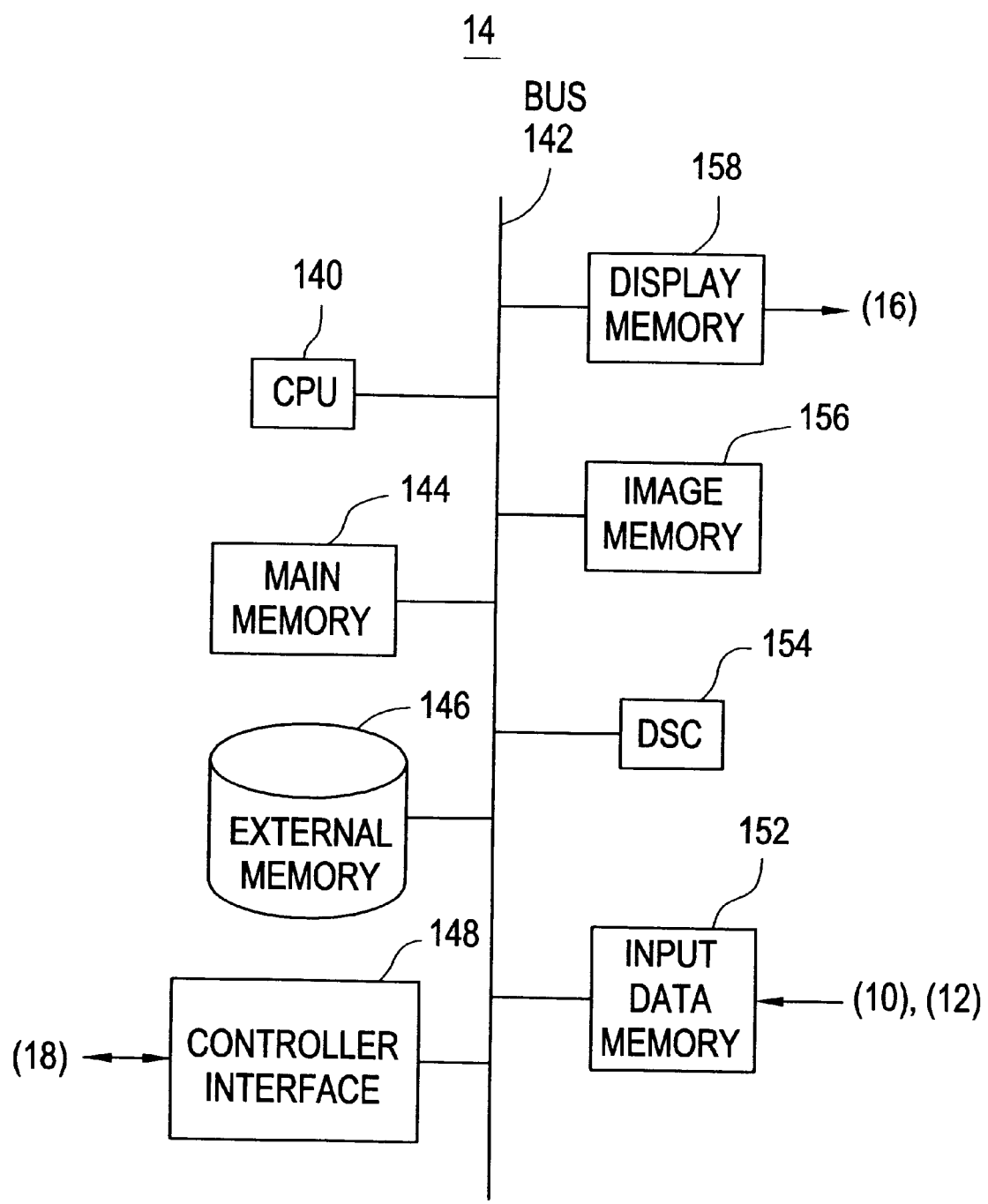

ULTRASONIC IMAGING APPARATUS

CROSS REFERENCE TO RELATED APPLICATIONS

This application claims the benefit of Japanese Application No. 2001-184678 filed Jun. 19, 2001.

BACKGROUND OF THE INVENTION

The present invention relates to an ultrasonic imaging method and an ultrasonic imaging apparatus, and particularly to an ultrasonic imaging method and an ultrasonic imaging apparatus both for scanning the inside of an object with an ultrasonic beam on a sound-ray sequential basis and thereby receiving echoes, and generating a dynamic image, based on a Doppler signal of the echoes.

Upon ultrasonic imaging, the inside of an object is scanned with an ultrasonic beam on a sound-ray sequential basis to receive echoes. A tomogram is generated based on an echo's intensity signal and displayed as a B-mode image. A dynamic image such as a blood flow or the like is generated using a Doppler signal of the echoes and displayed as a color Doppler image.

The degree of definition of an image varies according to a sound-ray density for scan. When the sound-ray density is made dense, the degree of definition thereof increases, whereas when the sound-ray density is made coarse, it is reduced. When a scan range is constant, a frame rate of an image is lowered when the sound-ray density is rendered dense, and the frame rate thereof is increased when the sound-ray density is rendered coarse. When the frame rate is constant, the scan range is narrowed when the sound-ray density is rendered dense, and the scan range is broadened when the sound-ray density is rendered coarse.

Since the above relationship is established between the sound-ray density, the scan range and the frame rate, it was difficult to enhance the degree of definition of an image without being affected by both the scan range and the frame rate. This particularly presents a problem upon such color Doppler imaging that a plurality of times of transmission and reception per sound ray are carried out.

SUMMARY OF THE INVENTION

Therefore, it is an object of the present invention to realize an ultrasonic imaging method and an ultrasonic imaging apparatus both capable of making both the maintenance of a scan range and a frame rate and high definition of an image compatible with each other.

(1) The invention according to one aspect for solving the problems is an ultrasonic imaging method for scanning the inside of an object with an ultrasonic beam on a sound-ray sequential basis and thereby receiving echoes, and generating a dynamic image, based on a Doppler signal of the echoes, characterized in that a sound-ray density for the scan is made to be nonuniform.

(2) The invention according to another aspect for solving the problems is an ultrasonic imaging apparatus for scanning the inside of an object with an ultrasonic beam on a sound-ray sequential basis and thereby receiving echoes, and generating a dynamic image, based on a Doppler signal of the echoes, characterized by being equipped with sound-ray density adjusting means for making a sound-ray density be nonuniform for the scan.

In the inventions according to the respective aspects described in (1) and (2), since the sound-ray density for the scan is made non-uniform, the sound-ray density of a required portion is rendered dense and other portions are rendered coarse, whereby the maintenance of a scan range and a frame rate and high definition of an image can be made compatible.

(3) The invention according to a further aspect for solving the problems is an ultrasonic imaging method for repeatedly scanning the inside of an object with an ultrasonic beam on a sound-ray sequential basis and thereby receiving echoes, and generating a dynamic image, based on a Doppler signal of the echoes, characterized in that a sound-ray density for the scan is made to be nonuniform while holding a range for the scan constant.

(4) The invention according to a still further aspect for solving the problems is an ultrasonic imaging apparatus for repeatedly scanning the inside of an object with an ultrasonic beam on a sound-ray sequential basis and thereby receiving echoes, and generating a dynamic image, based on a Doppler signal of the echoes, characterized by being equipped with sound-ray density adjusting means for making a sound-ray density be nonuniform for the scan while holding a range for the scan constant.

In the inventions according to the respective aspects described in (3) and (4), since the sound-ray density for the scan is made non-uniform while a scan range is being held constant, the sound-ray density of a required portion is rendered dense and other portions are made coarse, whereby the maintenance of the scan range and high definition of an image can be rendered compatible.

(5) The invention according to a still further aspect for solving the problems is an ultrasonic imaging method for repeatedly scanning the inside of an object with an ultrasonic beam on a sound-ray sequential basis and thereby receiving echoes, and generating a dynamic image frame, based on a Doppler signal of the echoes, characterized in that a sound-ray density for the scan is made to be nonuniform while holding a frame rate of the dynamic image frame constant.

(6) The invention according to a still further aspect for solving the problems is an ultrasonic imaging apparatus for repeatedly scanning the inside of an object with an ultrasonic beam on a sound-ray sequential basis and thereby receiving echoes, and generating a dynamic image frame, based on a Doppler signal of the echoes, characterized by being equipped with sound-ray density adjusting means for making a sound-ray density be nonuniform for the scan while holding a frame rate of the dynamic image frame constant.

In the inventions according to the respective aspects described in (5) and (6), since the sound-ray density for the scan is made nonuniform while the frame rate of the dynamic image frame is being held constant, the sound-ray density of a required portion is rendered dense and other portions are made coarse, whereby the maintenance of the frame rate and high definition of an image can be made compatible.

Preferably, the sound-ray density is rendered relatively dense at a bloodflow-existing portion and rendered relatively coarse at portions other than the portion in that a bloodflow image is brought into high definition.

The presence of the blood flow is preferably detected based on power of the Doppler signal in that the presence of the blood flow is reliably detected.

The presence of the blood flow is preferably detected based on a velocity determined from the Doppler signal in that the existence of the blood flow is reliably detected.

The presence of the blood flow is preferably detected based on a dispersion of the velocity obtained from the Doppler signal in that the presence of the blood flow is reliably detected.

The presence of the blood flow is preferably detected based on the velocity determined from the Doppler signal and the power of the Doppler signal in that the existence of the blood flow is detected more reliably.

The presence of the blood flow is preferably detected based on the dispersion of the velocity determined from the Doppler signal and the power of the Doppler signal in that the presence of the blood flow is detected more reliably.

The presence of the blood flow is preferably detected based on the velocity determined from the Doppler signal and its dispersion in that the presence of the blood flow is detected more reliably.

The presence of the blood flow is preferably detected based on the velocity determined from the Doppler signal and its dispersion, and the power of the Doppler signal in that the existence of the blood flow is detected still more reliably.

Preferably, the sound-ray density is rendered relatively dense at a portion specified by an external input and rendered relatively coarse at portions other than the portion in that the degree of freedom of a sound-ray density adjustment increases.

Therefore, an ultrasonic imaging method and an ultrasonic imaging apparatus each capable of making both the maintenance of a scan range and a frame rate, and high definition of an image compatible with each other can be realized.

Further objects and advantages of the present invention will be apparent from the following description of the preferred embodiments of the invention as illustrated in the accompanying drawings.

BRIEF DESCRIPTION OF THE DRAWINGS

FIG. 2 is a block diagram of a transmit-receive unit.

FIG. 3 is a typical diagram of sound ray scanning.

FIG. 4 is a typical diagram of sound ray scanning.

FIG. 6 is a block diagram of a B mode processor.

FIG. 7 is a block diagram of a Doppler processor.

FIG. 8 is a block diagram of an image processor.

DETAILED DESCRIPTION OF THE INVENTION

Figure 1:
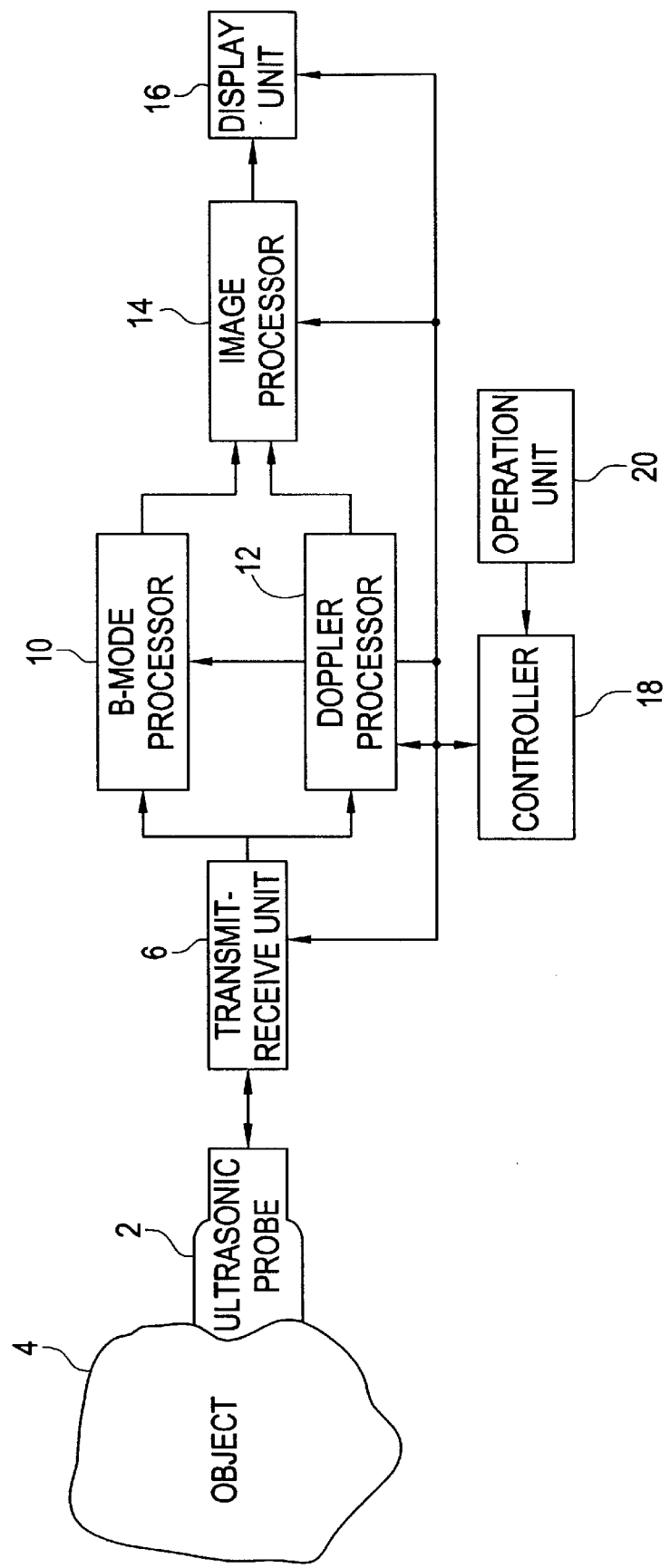
FIG. 1 is a block diagram of an apparatus illustrating one example of an embodiment of the present invention.

Embodiments of the present invention will hereinafter be described in detail with reference to the accompanying drawings. A block diagram of an ultrasonic imaging apparatus is shown in FIG. 1. The present apparatus is one example of an embodiment of the present invention. One example of the embodiment related to the apparatus of the present invention is illustrated according to the configuration of the present apparatus. One example of an embodiment related to a method of the present invention is shown according to the operation of the present apparatus.

As shown in FIG. 1, the present apparatus has an ultrasonic probe 2. The ultrasonic probe 2 has an array of a plurality of ultrasonic transducers unillustrated in the drawing. The individual ultrasonic transducers are formed of a piezoelectric material such as PZT (lead zirconate (Zr) titanate (Ti)) ceramics or the like. The ultrasonic probe 2 is used in contact with an object 4 by a user.

The ultrasonic probe 2 is connected to a transmit-receive unit 6. The transmit-receive unit 6 supplies a drive signal to the ultrasonic probe 2 to send an ultrasonic wave. The transmit-receive unit 6 receives an echo signal received by the ultrasonic probe 2.

A block diagram of the transmit-receive unit 6 is shown in FIG. 2. As shown in the same drawing, the transmit-receive unit 6 has a transmit timing generating unit 602. The transmit timing generating unit 602 periodically generates transmit timing signals and inputs the same to a transmit beamformer 604. The period of each transmit timing signal is controlled by a controller 18 to be described later.

The transmit beamformer 604 is used to perform beamforming for wave sending or transmission and generates a beamforming signal for forming an ultrasonic beam of a predetermined orientation, based on a transmit timing signal. The beamforming signal comprises a plurality of drive signals each added with a time difference associated with the orientation. The beamforming is controlled by the controller 18 to be described later. The transmit beamformer 604 inputs the transmit beamforming signal to a transmit-receive switch unit 606.

The transmit-receive switch unit 606 inputs the beamforming signal to its corresponding ultrasonic transducer array. In the ultrasonic transducer array, the plurality of ultrasonic transducers that constitute a transmit aperture, respectively generate ultrasonic waves each having a phase difference corresponding to the difference in time between the drive signals. An ultrasonic beam along sound rays oriented in a predetermined orientation is formed by combining wavefronts of these ultrasonic waves.

A receive beamformer 610 is connected to the transmit-receive switch unit 606. The transmit-receive switch unit 606 inputs a plurality of echo signals received by a receive aperture in the ultrasonic transducer array to the receive beamformer 610. The receive beamformer 610 is used to perform receive beamforming corresponding to transmit sound rays. The receive beamformer 610 applies time differences to a plurality of receive echoes to adjust phases and then adds them to thereby form echo receive signals along sound rays oriented in a predetermined orientation. The receive beamforming is controlled by the controller 18 to be described later.

The transmission of the ultrasonic beam is repeatedly performed at predetermined time intervals according to the transmit timing signals generated by the transmit timing generating unit 602. The transmit beamformer 604 and the receive beamformer 610 change the orientations of sound rays by predetermined amounts in accordance with the repetitive transmission. Consequently, the inside of the object 4 is successively scanned according to the sound rays.

The transmit-receive unit 6 configured in this way performs such scanning as shown in FIG. 3 by way of example. Namely, a two-dimensional area 206 is scanned in a θ direction with sound rays 202 extending in a z direction from a radiant point 200, a so-called sector scan is performed.

When transmit and receive apertures are formed using part of the ultrasonic transducer array, the apertures are successively moved along the array to thereby allow such scanning as shown in FIG. 4, for example. Namely, sound rays 202 emitted in a z direction from radiant points 200 are parallel translated or moved along a linear trajectory 204 to thereby scan a rectangular two-dimensional area 206 in an x direction, i.e., perform a so-called linear scan.

Figure 5:
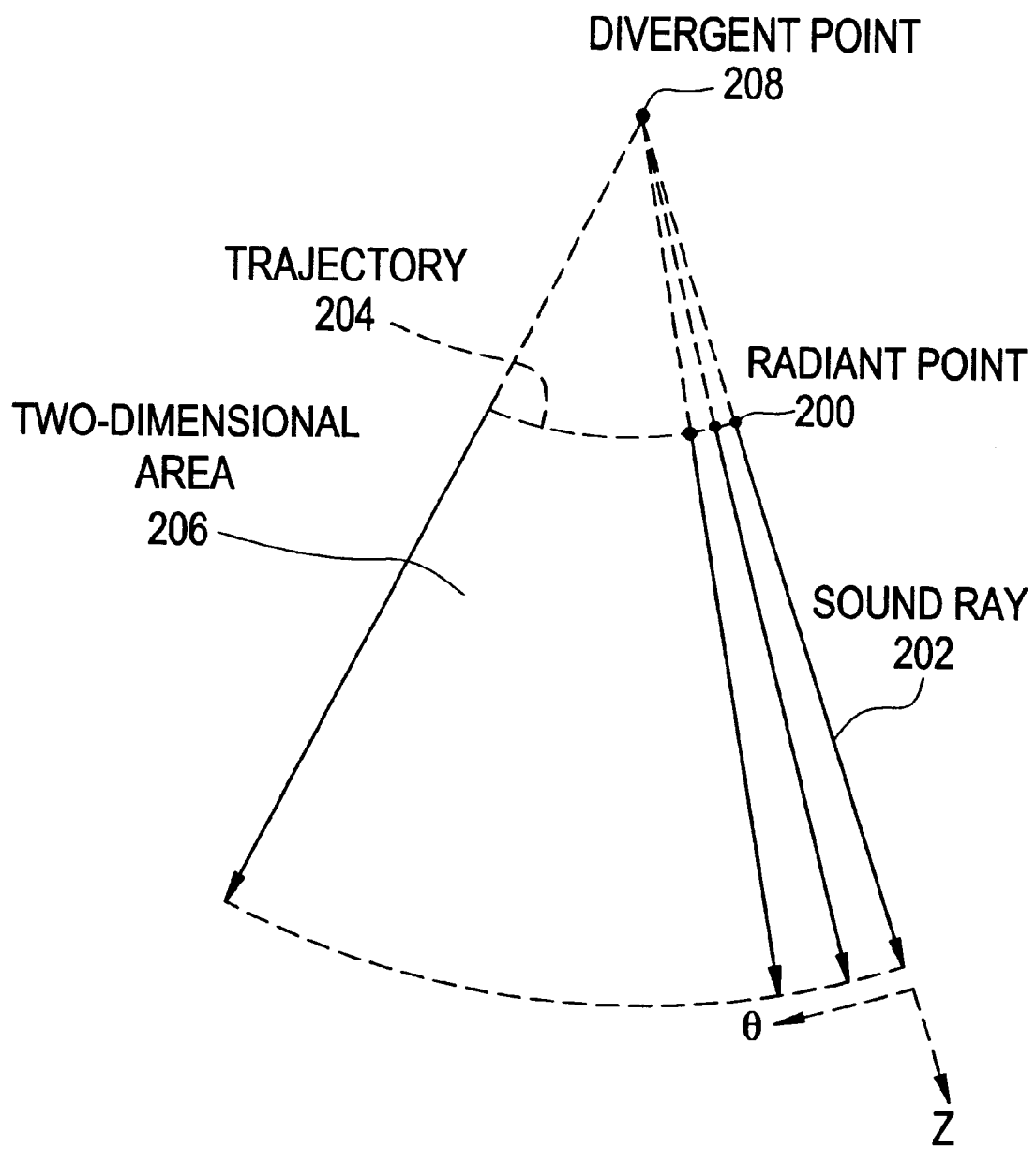
FIG. 5 is a typical diagram of sound ray scanning.

Incidentally, when the ultrasonic transducer array is a so-called convex array formed along a circular arc which extends out in an ultrasonic wave sending direction, radiant points 200 for sound rays 202 are moved along an arc trajectory 204 according to a sound-ray scan similar to the linear scan to thereby scan a sectorial two-dimensional area 206 in a θ direction as shown in FIG. 5 by way of example, whereby it is needless to say that a so-called convex scan can be carried out.

Such a scan is repeated under the control of the controller 18 to be described later. The density of each sound ray that scans the two-dimensional area 206, can be partly changed. When the sound-ray density is changed, the degree of definition of an image changes. Namely, as the sound-ray density is made denser, the degree of definition of the image is enhanced, whereas as the sound-ray density is made coarser, the degree of definition thereof is reduced.

The change in sound-ray density is performed by the transmit beamformer 604 and the receive beamformer 610 under the control of the controller 18 to be described later. A portion comprising the controller 18, the transmit beamformer 604 and the receive beamformer 610 shows one example of an embodiment of sound-ray density adjusting means in the present invention.

The transmit-receive unit 6 is connected to a B mode processor 10 and a Doppler processor 12. An echo receive signal set for each sound ray, which is outputted from the transmit-receive unit 6, is inputted to the B mode processor 10 and the Doppler processor 12.

The B mode processor 10 forms B-mode image data. As shown in FIG. 6, the B mode processor 10 is equipped with a logarithmic amplifying unit 102 and an envelope detection unit 104. In the B mode processor 10, the logarithmic amplifying unit 102 logarithmically amplifies each echo receive signal, and the envelope detection unit 104 detects an envelope thereof to obtain a signal indicative of the intensity of an echo at each reflecting point on a sound ray, i.e., an A scope signal, thereby forming B-mode image data with respective instantaneous amplitudes of the A scope signal as luminance values respectively.

The Doppler processor 12 is used to form Doppler image data. The Doppler image data includes flow velocity data, distributed data and power data to be described later.

As shown in FIG. 7, the Doppler processor 12 includes a quadrature detection unit 120, an MTI filter (moving object indication filter) 122, an auto-correlation calculating unit 124, an average flow velocity calculating unit 126, a dispersion calculating unit 128 and a power calculating unit 130.

The Doppler processor 12 effects quadrature detection on each echo receive signal through the use of the quadrature detection unit 120, and performs MTI processing thereof through the use of the MTI filter 122 to thereby obtain a Doppler signal of each echo. Further, the Doppler processor 12 effects an auto-correlation calculation on a signal outputted from the MTI filter 122, through the use of the auto-correlation calculating unit 124. The Doppler processor 12 determines an average flow velocity V from the result of the auto-correlation calculation through the use of the average flow velocity calculating unit 126. The Doppler processor 12 determines a dispersion T of a flow velocity from the result of the auto-correlation calculation through the use of the dispersion calculating unit 128. Further, the Doppler processor 12 determines power PW of the Doppler signal from the result of the auto-correlation calculation through the use of the power calculating unit 130. The average flow velocity is also hereinafter called simply a flow velocity. Further, the dispersion of the flow velocity is also called simply dispersion, and the power of the Doppler signal is also called simply power.

Respective data indicative of the flow velocity V, dispersion T and power PW of an echo source moved within the object 4 are obtained every sound rays by the Doppler processor 12. These data indicate the flow velocity, dispersion and power of each of points (pixels) on sound rays. Incidentally, the flow velocity is obtained as a component in the direction of each sound ray. A distinction is made between the direction in which the object approaches the ultrasonic probe 2 and the direction in which it moves away therefrom.

The B mode processor 10 and the Doppler processor 12 are connected to an image processor 14. The image processor 14 produces a B-mode image and a Doppler image respectively, based on data respectively inputted from the B mode processor 10 and the Doppler processor 12.

As shown in FIG. 8, the image processor 14 has a central processing unit (CPU: Central Processing Unit) 140. A main memory 144, an external memory 146, a controller interface 148, an input data memory 152, a digital scan converter (DSC: Digital Scan Converter) 154, an image memory 156 and a display memory 158 are connected to the CPU 140 by a bus 142.

At least one program executed by the CPU 140 is stored in the external memory 146. Various data used upon the execution of the program by the CPU 140 are also stored in the external memory 146.

The CPU 140 loads the corresponding program into the main memory 144 through the external memory 146 and executes it, thereby performing predetermined image processing. The CPU 140 performs the transmission and reception of control signals to and from the controller 18 to be described later through the controller interface 148.

B-mode image data and Doppler image data inputted for each sound ray from the B mode processor 10 and the Doppler processor 12 are respectively stored in the input data memory 152. The data stored in the input data memory 152 are scanned and converted by the DSC154 and stored in the image memory 156. The data of the image memory 156 are outputted to a display unit 16 through the display memory 158.

The display unit 16 is connected to the image processor 14. The display unit 16 is supplied with an image signal from the image processor 14 and displays an image, based on the image signal. The display unit 16 comprises a graphic display or the like using a CRT (cathode-ray tube) capable of displaying a color image thereon.

The controller 18 is connected to the transmit-receive unit 6, B mode processor 10, Doppler processor 12, image processor 14 and display unit 16 referred to above. The controller 18 supplies control signals to their respective parts to control their operations. Various notification signals are inputted to the controller 18 from the respective controlled parts. A B mode operation and a Doppler mode operation are executed under the control of the controller 18.

Figure 9:
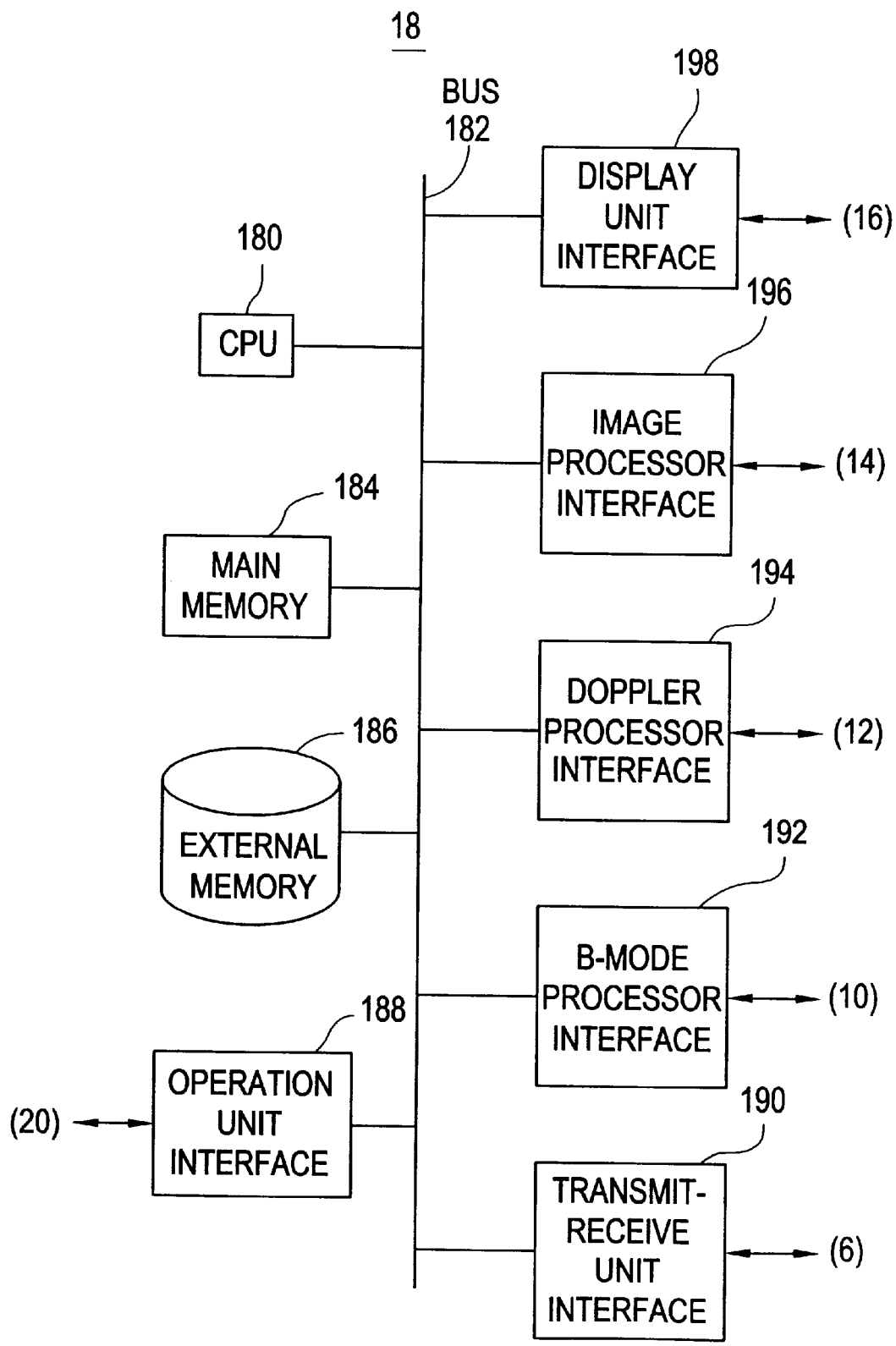
FIG. 9 is a block diagram of a controller.

As shown in FIG. 9, the controller 18 has a CPU180. A main memory 184, an external memory 186, an operation unit interface 188, a transmit-receive unit interface 190, a B mode processor interface 192, a Doppler processor interface 194, an image processor interface 196 and a display unit interface 198 are connected to the CPU180 by a bus 182.

At least one program executed by the CPU180 is stored in the external memory 186. Various data used upon the execution of the program by the CPU180 are also stored in the external memory 186.

The CPU180 loads the corresponding program into the main memory 184 through the external memory 186 and executes it, thereby performing predetermined control. The CPU180 performs the transmission and reception of control signals to and from the respective parts through the operation unit interface 188 through the display unit interface 198 in the process of program execution.

An operation unit 20 is connected to the controller 18. The operation unit 20 is controlled by a user to input suitable instructions and information to the controller 18. The operation unit 20 is provided with, for example, a keyboard, a pointing device and other operation devices.

An imaging operation of the present apparatus will be described. The user brings the ultrasonic probe 2 into contact with a desired point of the object 4. The user operates the operation unit 20 to carry out an imaging operation utilizing a B mode and a Doppler mode in combination.

Consequently, B-mode imaging or Doppler mode imaging are carried out on a time-sharing basis under the control of the controller 18. Namely, a mixed scan of the B mode and the Doppler mode is carried out at such a rate that the scan of the B mode is performed once each time the scan of the Doppler mode is carried out by a predetermined number of times.

In the B mode, the transmit-receive unit 6 scans the inside of the object 4 on a sound-ray sequential basis through the ultrasonic probe 2 and receives their echoes one by one. The B mode processor 10 logarithmically amplifies an echo receive signal inputted from the transmit-receive unit 6 through the use of the logarithmic amplifying unit 102, and detects an envelope thereof through the use of the envelope detection unit 104 to obtain an A scope signal, thereby forming B-mode image data set every sound rays, based on it.

The image processor 14 allows the input data memory 152 to store the B-mode image data set every sound rays, inputted from the B mode processor 10. Thus, sound-ray data spaces about the B-mode image data are formed within the input data memory 152.

In the Doppler mode, the transmit-receive unit 6 scans the inside of the object 4 on a sound-ray sequential basis through the ultrasonic probe 2 and receives their echoes one by one. At this time, a plurality of times of transmission of ultrasonic waves and reception of echoes per sound ray are carried out.

The Doppler processor 12 effects quadrature detection on each echo receive signal through the use of the quadrature detection unit 120 and effects MTI processing thereof through the use of the MTI filter 122. The Doppler processor 12 determines auto-correlation with the auto-correlation calculating unit 124 and determines a flow velocity V from the result of the auto-correlation through the use of the flow velocity calculating unit 126. Further, the Doppler processor 12 determines a dispersion T through the use of the dispersion calculating unit 128 and obtains power PW through the use of the power calculating unit 130. These calculated values respectively result in data indicative of the flow velocity, dispersion and power of an echo source every sound rays and pixels.

The image processor 14 allows the input data memory 152 to store the respective Doppler image data set every sound rays and pixels, which are inputted from the Doppler processor 12. Thus, sound-ray data spaces about the respective Doppler image data are respectively formed within the input data memory 152.

The CPU 140 scans and converts the B-mode image data and the respective Doppler image data of the input data memory 152 through the use of the DSC154 and writes them into the image memory 156

At this time, the Doppler image data are respectively written as flow-velocity distribution image data utilizing the flow velocity V and the dispersion T in combination, power Doppler image data using the power PW or power Doppler image data with dispersion, utilizing the power PW and the dispersion T in combination, and dispersion image data using the dispersion T.

The CPU 140 writes the B-mode image data and the respective Doppler image data into discrete areas. An image based on these B-mode image data and Doppler image data is displayed on the display unit 16.

The B-mode image shows a tomogram of an in-vivo tissue on a sound-ray scanning plane. Of color Doppler images, a flow velocity distribution image results in an image indicative of a two-dimensional distribution of a flow velocity of an echo source. In the present image, display colors are made different according to the direction of a flow. The display colors are made different in luminance according to the flow velocity. The color-mixed amount of predetermined colors is enhanced according to the dispersion, whereby the purity of each display color is changed. The flow velocity distribution image is also called a color flow mapping (CFM: Color Flow Mapping) image.

A power Doppler image results in an image indicative of a two-dimensional distribution of power. The location of the echo source exercised according to the image is shown. The luminance of each display color for the image corresponds to the power. When the power is utilized in combination with the dispersion, the color-mixed amount of predetermined colors is enhanced according to the dispersion to change the purity of each display color.

A dispersion image results in an image indicative of a two-dimensional distribution of dispersed values. This image also indicates the location of a moving echo source, whose velocity has a dispersion. The luminance of each display color corresponds to the magnitude of the dispersion. A blood flow becomes major as one in which the velocity has the dispersion. Thus, the blood flow can be distinguished from the motion of a tissue such as valves of the heart.

When these images are displayed on the display unit 16, the display memory 158 combines the images with the B-mode image, and the combined image is displayed on the display unit 16, whereby a color Doppler image evident in position relationship with an in-vivo tissue can be observed.

Figure 10:
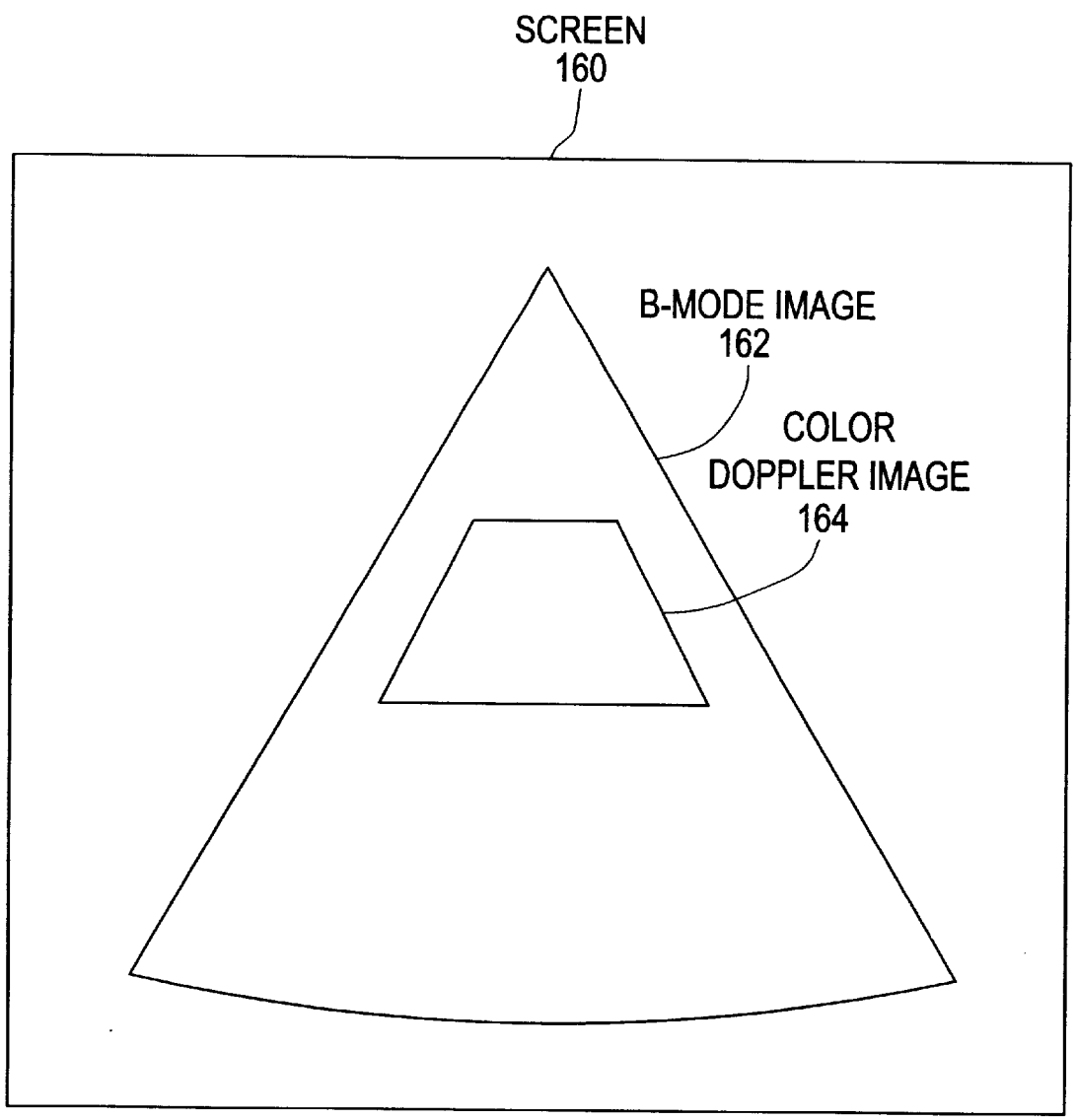
FIG. 10 is a simplified diagram showing one example of a screen displayed on a display unit.

An example of a screen on which such an image is displayed, is shown in FIG. 10 in the form of a schematic illustration. As shown in the same drawing, a B-mode image 162 shot or imaged by a sector scan is displayed on a screen 160. A color Doppler image 164 is displayed on the B-mode image 162. However, the color Doppler image 164 is represented by a boundary of a display area. Any of a CFM image, a power Doppler image or a dispersion image is displayed as the color Doppler image 164. Whether any should be displayed, depends on the designation of a user.

An area for the object 4 corresponding to the display area is cable of being shot or imaged with a non-uniform sound-ray density partly changed in its density. The sound-ray density is changed such that a sound-ray density of a bloodflow-existing portion is made denser than at portions other than it.

Figure 11:
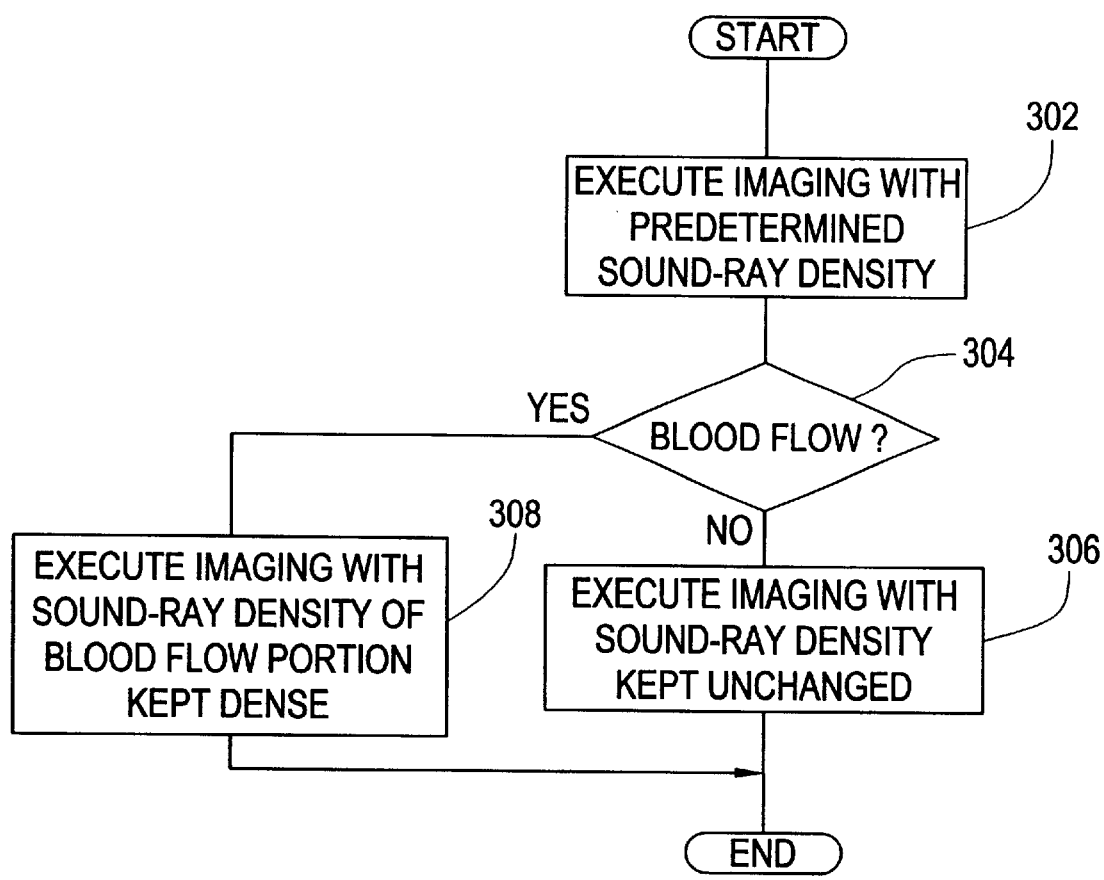
FIG. 11 is a flow chart showing operation of the apparatus illustrative of one example of the embodiment of the present invention.

Operation at the time that the area for the object 4 is imaged with the nonuniform sound-ray density is shown in FIG. 11 according to a flow chart. As shown in the same drawing, shooting or imaging is done with a predetermined sound-ray density in Step 302. In an initial state, the predetermined sound-ray density is a uniform sound-ray density. Color Doppler images obtained by such imaging are stored in the image memory 156. The color Doppler images include three types of a CFM image, a power Doppler image and a dispersion image.

Next, in Step 304, it is determined whether a blood flow exists within an imaging area. The presence or absence of the blood flow is determined based on the power of a Doppler signal, for example. Namely, when the power of the Doppler signal is greater than or equal to a predetermined threshold value, the blood flow is judged to exist. When it is less than the threshold value, the blood flow is judged not to exist. Such judgments are done by the CPU 140 in the image processor 14. The CPU 140 detects the location of a pixel value having power greater than or equal to a threshold value with respect to each of the power Doppler images stored in the image memory 156. The CPU 140 is one example of an embodiment of bloodflow detecting means according to the present invention.

The presence or absence of the blood flow may be determined based on the flow velocity in place of the power. In this case, the CPU 140 detects the location of a pixel value having a flow velocity greater than or equal to a threshold value with respect to the CFM image stored in the image memory 156. This may be determined based on dispersion. In this case, the CPU 140 detects the location of a pixel value having a dispersion greater than or equal to a threshold value with respect to the dispersion image stored in the image memory 156.

With respect to a combination of any two of power, a flow velocity and a dispersion, or a combination of all, the presence or absence of the blood flow may be detected according to a decision based on their threshold values. Highly reliable bloodflow detection can be carried out.

When no blood flow is detected, imaging is carried out in Step 306 while a sound-ray density remains unchanged. The imaging is performed in this state while no blood flow is being detected. When the blood flow is detected, imaging in which the sound-ray density of a bloodflow portion is made dense, is carried out in Step 308.

This imaging is performed by controlling the transmit beamformer 604 and the receive beamformer 610 of the transmit-receive unit 6 by means of the controller 18. Based on a signal indicative of the location of a blood flow, which is inputted from the image processor 14, the controller 18 controls the transmit beamformer 604 and the receive beamformer 610 in such a manner that the sound-ray density is made dense at the portion where the blood flow exists. Subsequently, the imaging is carried in this state.

Figure 12:
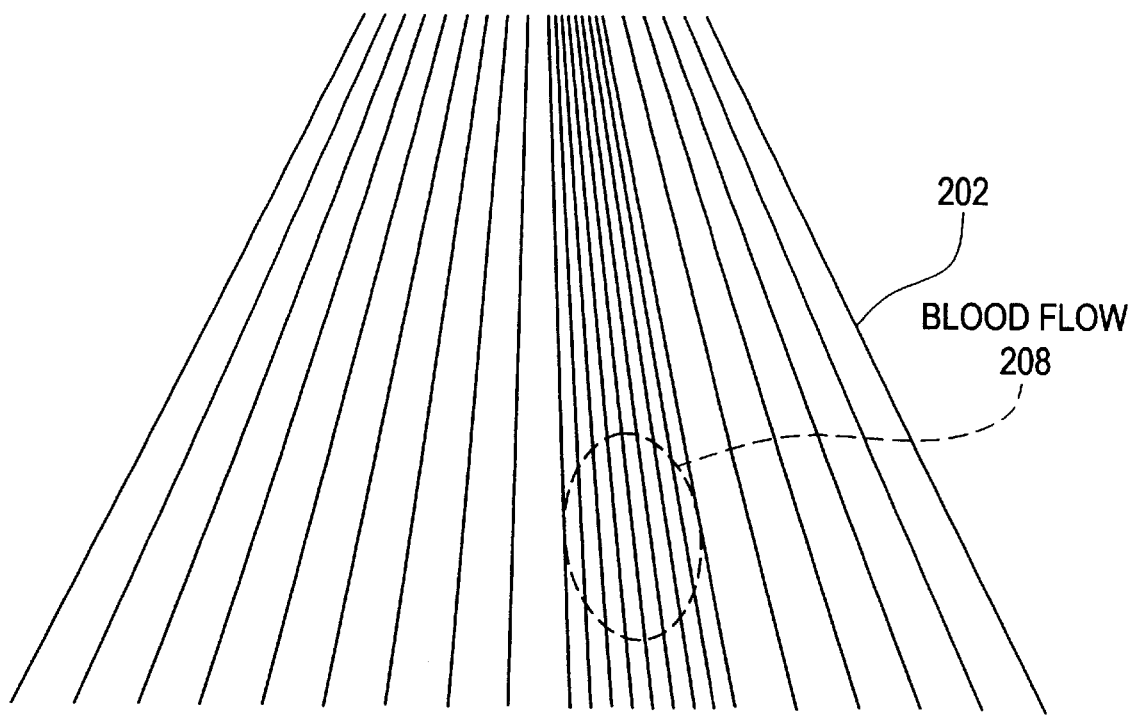
FIG. 12 is a typical diagram of sound ray scanning.

Thus, a portion where a blood flow 208 exists, is scanned with sound rays increased in density as shown in FIG. 12 by way of example, so that an image good in definition degree about the blood flow 208 can be obtained. Portions other than the bloodflow-existing portion are scanned in sound-ray densities coarser than at the bloodflow-existing portion. Thus, although images of the portions other than the bloodflow-existing portion are degraded in definition degree, no problem arises because they are not intended for user'interest.

When the sound-ray density of the bloodflow-existing portion is raised, the sound-ray densities of other portions may be set lower than an initial value correspondingly. Thus, the number of sound rays that scan each imaging area, can be kept constant. Keeping the number of the sound rays constant makes it possible to hold a frame rate constant. It is also possible to keep a scan range constant.

When the sound-ray density is sufficiently dense in the initial state, the sound-ray densities of other portions may be lowered while the sound-ray density of the bloodflow portion is kept intact. Consequently, the number of sound rays that scan an imaging range is reduced and hence a frame rate is enhanced.

When the sound-ray density is coarse in the initial state, the sound-ray density of the bloodflow portion is raised and the sound-ray densities of other portions may be kept intact. Thus, the number of sound rays that scan an imaging range, increases and a frame rate is lowered. However, no problem presents if it falls within an allowable range.

Adjustments to the sound-ray density referred to above are automatically carried out at pre-fixed predetermined time intervals. As an alternative to the automatic adjustments, or in addition to it, the adjustments may be performed at the time specified by a user through the use of a press button or the like. Thus, even if the position of the blood flow 208 changes within the imaging area due to body motion of the object 4, the movement of the ultrasonic probe 2, etc., a sound-ray density adjustment adapted to the updated position can be performed.

Figure 13:
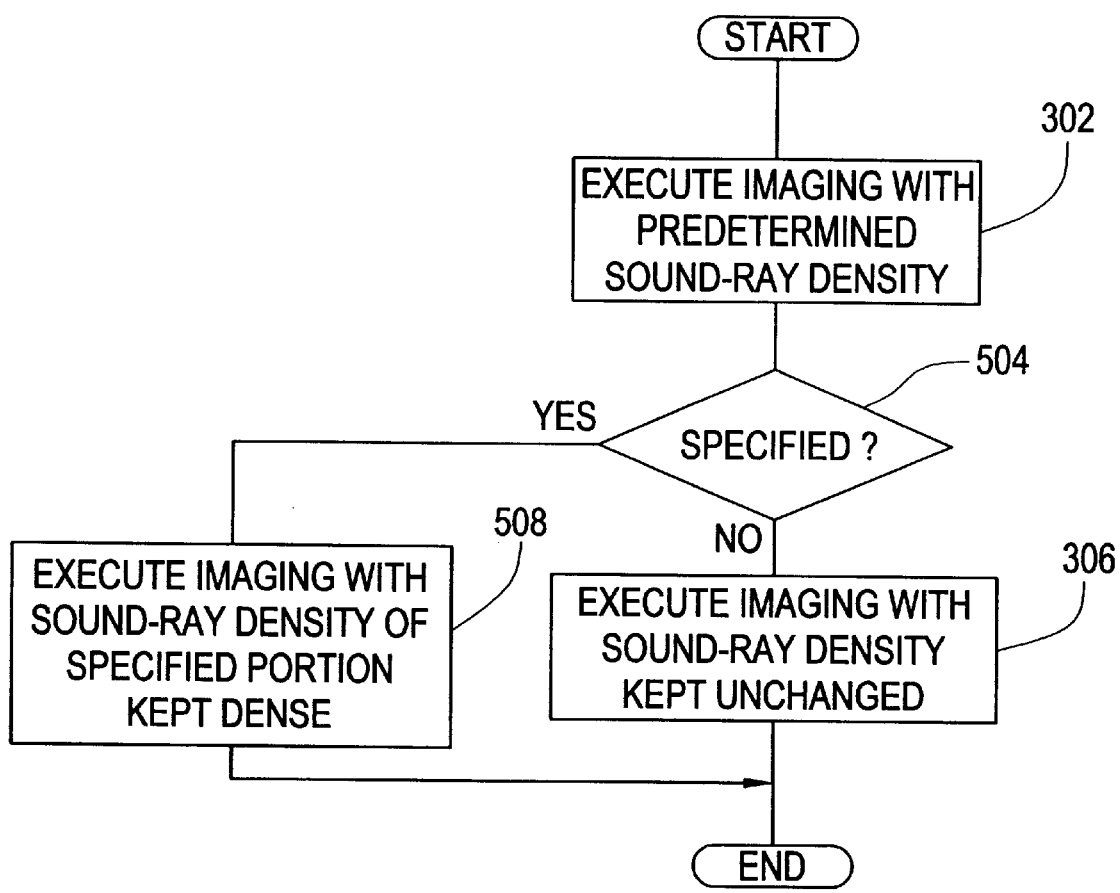
FIG. 13 is a flow chart showing another operation of the apparatus illustrative of one example of the embodiment of the present invention.

The user may specify or designate a portion made dense in sound-ray density on a displayed screen by means of a pointing device or the like. A flow chart for describing operation in this case is shown in FIG. 13. This flow chart is identical to the flow chart shown in FIG. 11 except for Steps 504 and 508.

As shown in the same drawing, the presence or absence of the designation of the portion is determined in Step 504. When the portion made dense in sound-ray density is specified, the sound-ray density of the specified portion is rendered dense in Step 508. Coarse and dense adjustments to the sound-ray density are similar to the above. Thus, the portion in which the blood flow 208 exists, can be imaged with dense sound rays in a manner similar to one shown in FIG. 12 by way of example. Incidentally, this technique can be applied not only to the case where the sound-ray density of the bloodflow portion is raised, but also to the case where a desired portion at a B-mode image, for example, is imaged with high definition in particular, and the like.

While the present invention has been described above based on the examples of the preferred embodiments, those having normal knowledge in the technical field to which the present invention belongs, are capable of effecting various changes and substitutions or the like on the examples of the above embodiments without departing from the technical scope of the present invention. Accordingly, all the embodiments, which belong to the claims, fall within the technical scope of the present invention as well as the examples of the above embodiments.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic imaging apparatus for scanning the inside of an object with an ultrasonic beam on a sound-ray sequential basis and thereby receiving echoes, and generating a dynamic image, based on a Doppler signal of the echoes, comprising:

a sound-ray density adjusting device for making a sound-ray density be nonuniform for the scan.

2. An ultrasonic imaging apparatus according to claim 1, wherein said sound-ray density adjusting device sets the sound-ray density relatively dense at a portion where a blood flow exists, and sets the sound-ray density relatively coarse at portions other than the portion.

3. An ultrasonic imaging apparatus according to claim 2, including a blood flow detecting device for detecting the presence of the blood flow, based on power of the Doppler signal.

4. An ultrasonic imaging apparatus according to claim 2, including a blood flow detecting device for detecting the presence of the blood flow, based on a velocity obtained from the Doppler signal.

5. An ultrasonic imaging apparatus according to claim 2, including a blood flow detecting device for detecting the presence of the blood flow, based on a dispersion of the velocity obtained from the Doppler signal.

6. An ultrasonic imaging apparatus according to claim 2, including a blood flow detecting device for detecting the presence of the blood flow, based on the velocity obtained from the Doppler signal and the power of the Doppler signal.

7. An ultrasonic imaging apparatus according to claim 2, including a blood flow detecting device for detecting the presence of the blood flow, based on the dispersion of the velocity obtained from the Doppler signal and the power of the Doppler signal.

8. An ultrasonic imaging apparatus according to claim 2, including a blood flow detecting device for detecting the presence of the blood flow, based on the velocity obtained from the Doppler signal and its dispersion.

9. An ultrasonic imaging apparatus according to claim 2, including a blood flow detecting device for detecting the presence of the blood flow, based on the velocity obtained from the Doppler signal and its dispersion, and the power of the Doppler signal.

10. An ultrasonic imaging apparatus according to claim 1, wherein said sound-ray density adjusting device sets the sound-ray density relatively dense at a portion specified by an external input and sets the sound-ray density relatively coarse at portions other than the portion.

11. An ultrasonic imaging apparatus for repeatedly scanning the inside of an object with an ultrasonic beam on a sound-ray sequential basis and thereby receiving echoes, and generating a dynamic image, based on a Doppler signal of the echoes, comprising:

a sound-ray density adjusting device for making a sound-ray density be nonuniform for the scan while holding a range for the scan constant.

12. An ultrasonic imaging apparatus according to claim 11, wherein said sound-ray density adjusting device sets the sound-ray density relatively dense at a portion where a blood flow exists, and sets the sound-ray density relatively coarse at portions other than the portion.

13. An ultrasonic imaging apparatus according to claim 12, including a blood flow detecting device for detecting the presence of the blood flow, based on power of the Doppler signal.

14. An ultrasonic imaging apparatus according to claim 12, including a blood flow detecting device for detecting the presence of the blood flow, based on a velocity obtained from the Doppler signal.

15. An ultrasonic imaging apparatus according to claim 12, including a blood flow detecting device for detecting the presence of the blood flow, based on a dispersion of the velocity obtained from the Doppler signal.

16. The ultrasonic imaging apparatus as claimed in claim 12, including a blood flow detecting device for detecting the presence of the blood flow, based on the velocity obtained from the Doppler signal and its dispersion, and the power of the Doppler signal.

17. An ultrasonic imaging apparatus according to claim 11, wherein said sound-ray density adjusting device sets the sound-ray density relatively dense at a portion specified by an external input and sets the sound-ray density relatively coarse at portions other than the portion.

18. An ultrasonic imaging apparatus for repeatedly scanning the inside of an object with an ultrasonic beam on a sound-ray sequential basis and thereby receiving echoes, and generating a dynamic image frame, based on a Doppler signal of the echoes, comprising:

a sound-ray density adjusting device for making a sound-ray density be nonuniform for the scan while holding a frame rate of the dynamic image frame constant.

19. An ultrasonic imaging apparatus according to claim 18, wherein said sound-ray density adjusting device sets the sound-ray density relatively dense at a portion where a blood flow exists, and sets the sound-ray density relatively coarse at portions other than the portion.

20. An ultrasonic imaging apparatus according to claim 18, wherein said sound-ray density adjusting device sets the sound-ray density relatively dense at a portion specified by an external input and sets the sound-ray density relatively coarse at portions other than the portion.

* * * * *

UNITED STATES PATENT AND TRADEMARK OFFICE
CERTIFICATE OF CORRECTION

PATENT NO.     : 6,602,196 B2                                              Page 1 of 1
DATED          : August 5, 2003
INVENTOR(S)    : Yoichi Suzuki et al.

It is certified that error appears in the above-identified patent and that said Letters Patent is hereby corrected as shown below:

Column 11,
Line 10, delete "the" insert therefor -- an --.
Lines 19 and 54, delete "relatively" insert therefor -- to be more --.
Line 20, delete "exists, and sets the sound-ray density relatively coarse at portions other than the portion." insert therefor -- exists than at other portions. --.
Line 55, delete "and sets the sound-ray density relatively coarse at portions other than the portion." insert therefor -- than at other other portions. --.

Column 12,
Lines 2 and 38, delete "the" insert therefor -- an --.
Lines 11, 34, 47 and 52, delete "relatively" insert therefor -- to be more --.
Lines 12 and 48, delete "exists, and sets the sound-ray density relatively coarse at portions other than the portion." insert therefor -- exists than at other portions. --.
Lines 35 and 53, delete "and sets the sound-ray density relatively coarse at portions other than the portion." insert therefor -- than at other other portions. --.

Signed and Sealed this

Twenty-third Day of March, 2004

JON W. DUDAS
*Acting Director of the United States Patent and Trademark Office*